United States Patent
Han et al.

(10) Patent No.: US 12,023,370 B2
(45) Date of Patent: Jul. 2, 2024

(54) COMPOSITION FOR THE TREATMENT OF COVID-19 INFECTION, AND A METHOD OF TREATMENT

(71) Applicants: Qinghong Han, San Diego, CA (US); Robert Hoffman, San Diego, CA (US)

(72) Inventors: Qinghong Han, San Diego, CA (US); Robert Hoffman, San Diego, CA (US)

(73) Assignee: ANTICANCER INC., San Diego, CA (US)

( * ) Notice: Subject to any disclaimer, the term of this patent is extended or adjusted under 35 U.S.C. 154(b) by 16 days.

(21) Appl. No.: 17/365,925

(22) Filed: Jul. 1, 2021

(65) Prior Publication Data

US 2021/0330767 A1 Oct. 28, 2021

Related U.S. Application Data

(63) Continuation-in-part of application No. 17/225,677, filed on Apr. 8, 2021, now Pat. No. 11,371,036.

(51) Int. Cl.
| | |
|---|---|
| *A61K 38/51* | (2006.01) |
| *A61K 31/245* | (2006.01) |
| *A61K 31/336* | (2006.01) |
| *A61K 31/675* | (2006.01) |

(52) U.S. Cl.
CPC .......... *A61K 38/51* (2013.01); *A61K 31/245* (2013.01); *A61K 31/336* (2013.01); *A61K 31/675* (2013.01); *C12Y 404/01011* (2013.01)

(58) Field of Classification Search
CPC .... A61K 38/51; A61K 31/245; A61K 31/336; A61K 31/675; A61K 38/55; A61K 45/06; A61K 9/0095; A61K 2300/00; C12Y 404/01011; A61P 3/10; A61P 35/00; C12N 9/88
See application file for complete search history.

(56) References Cited

U.S. PATENT DOCUMENTS

| | | | | |
|---|---|---|---|---|
| 11,371,036 | B2 * | 6/2022 | Han | A61K 9/0053 |
| 2005/0031606 | A1 * | 2/2005 | Tan | A61K 31/135 |
| | | | | 424/94.4 |
| 2014/0205583 | A1 * | 7/2014 | Yagi | A61K 31/74 |
| | | | | 424/94.3 |
| 2019/0153421 | A1 * | 5/2019 | Han | A61K 31/675 |
| 2019/0153521 | A1 * | 5/2019 | Mitchell | C12Q 1/6837 |

OTHER PUBLICATIONS

McKee DL, et al "Candidate drugs against SARS-CoV-2 and COVID-19" Pharmacological Research, Jul. 2020 (epub Apr. 29, 2020), 157(104859),9 pp.; doi: 10.1016/j.phrs.2020.104859 (Year: 2020).*

Nitulescu GM, et al "Comprehensive analysis of drugs to treat SARS CoV 2 infection: Mechanistic insights into current COVID 19 therapies (Review)" Int J Molec Med, 2020 (ePub May 18, 2020), 46,pp. 467-488; doi:10.3892/ijmm.2020.4608 (Year: 2020).*

Steuten K, et al "Challenges for targeting SARS-CoV-2 proteases as a therapeutic strategy for COVID-19 " bioRxiv, Nov. 23, 2020, 32pp; doi: 10.1101/2020.11.21.392753v1 (also in ACS Infectious Diseases as doi: 10.1021/acsinfecdis.0c00815). (Year: 2020).*

Kim JC, et al "Coronavirus protein processing and RNA synthesis is inhibited by the cysteine proteinase inhibitor E64d" Virology, Apr. 1, 1995, 208(1),1-8. (PMID: 11831690); doi: 10.1006/viro.1995.1123. (Year: 1995).*

Hoffman M, et al "SARS-CoV-2 Cell Entry Depends on ACE2 and TMPRSS2 and Is Blocked by a Clinically Proven Protease Inhibitor" Cell, Apr. 16, 2020 (ePub Mar. 5, 2020) , 181(2),271-280 . . . e8; doi: 10.1016/j.cell.2020.02.052. (Year: 2020).*

Mykytryn AZ, et al "SARS-CoV-2 entry into human airway organoids is serine protease-mediated and facilitated by the multibasic cleavage site" eLife: Microbiology and Infectious Disease Jan. 4, 2021, 10(e64508); 23 pp;doi: 10.7554/eLife.64508. (Year: 2021).*

Hoffman RM and Han Q "Oral Methioninase for Covid-19 Methionine-restriction Therapy" in vivo 34(3 Suppl),Jun. 2020,pp. 1593-1596; doi:10.21873/invivo. 11948 (PMID: 32503816). (Year: 2020).*

Kumrungsee T, et al "Potential Role of Vitamin B6 in Ameliorating the Severity of COVID-19 and Its Complications" Front Nutr,7, Oct. 29, 2020, ; doi: 10.3389/fnut.2020.562051. (Year: 2020).*

Shakoor H, et al "Be well: A potential role for vitamin B in COVID-19" Maturitas, Feb. 2021 (ePub Aug. 15, 2020), 144,pp. 108-111; doi: 10.1016/j.maturitas.2020.08.007; PMID: 32829981. (Year: 2020).*

Hoffman RM and Han Q "Oral Methioninase for Covid-19 Methionine-restriction Therapy" in vivo </i>34(3 Suppl),Jun. 2020, pp. 1593-1596; doi:10.21873/invivo.11948 (PMID: 32503816). (Year: 2020).*

Kumrungsee T, et al "Potential Role of Vitamin B6 in Ameliorating the Severity of COVID-19 and Its Complications" Front Nutr</i>,7, Oct. 29, 2020, ; doi:10.3389/fnut.2020.562051, (Year: 2020).*

Shakoor H, et al "Be well: A potential role for vitamin B in COVID-19" Maturitas</i>, Feb. 2021 (ePub Aug. 15, 2020),144,pp. 108-111; doi:10.1016/j.maturitas.2020.08.007; PMID: 32829981 (Year: 2020).*

Hoffman RM, et al "SARS-CoV-2 Cell Entry Depends on ACE2 and TMPRSS2 and Is Blocked by a Clinically Proven Protease Inhibitor" Cell</i>, Apr. 16, 2020 (ePub Mar. 5, 2020) ,181(2),271-280 . . . e8; doi: 10.1016/j.cell.2020.02.052. (Year: 2020).*

* cited by examiner

*Primary Examiner* — Aaron J Kosar
(74) *Attorney, Agent, or Firm* — Barry Choobin; Patent 360

(57) ABSTRACT

Oral composition and a method for the treatment of coronaviruses infections in humans and animals. The method includes the steps of administering orally a methionine cleaving-enzyme; administering orally or parentally a protease inhibitor; and orally administering pyridoxal-L-phosphate in a fluid.

18 Claims, No Drawings

COMPOSITION FOR THE TREATMENT OF COVID-19 INFECTION, AND A METHOD OF TREATMENT

CROSS-REFERENCE TO RELATED APPLICATION

This application is a continuation-in-part of a U.S. Non-Provisional application Ser. No. 17/225,677 filed on Apr. 8, 2021, which is a divisional application of a U.S. Non-Provisional application Ser. No. 16/165,879, filed Oct. 10, 2018, which claims priority from a U.S. Provisional Patent Application Ser. No. 62/574,693 filed Oct. 19, 2017, the entire contents of the above three applications are incorporated herein by reference.

FIELD OF INVENTION

This invention relates to a composition and a method for the treatment of Covid-19 infection and more particularly, the invention relates to an orally administered composition including a methoninase enzyme and protease inhibitor for the treatment of Covid-19 infection.

BACKGROUND

SARS (severe acute respiratory syndrome) coronaviruses abbreviated as (SARS-CoV) were identified in 2003. Primarily bats are the reservoir for SARS-CoV, which is known to spread to humans. These viruses generally target the respiratory system of a patient and show influenza-like symptoms. The symptoms include fever, malaise, myalgia, headache, diarrhea, and shivering (rigors). Fever is the most frequently reported symptom, however, none of the symptoms is specific for SARS-CoV. COVID-19, a newly discovered virus of the SARS coronaviruses family that caused a global pandemic resulting in the loss of millions of human lives and a global shutdown. Symptoms of COVID-19 can range from mild illness to pneumonia, renal dysfunction, and multi-organ failure. Currently, there is no specific antiviral treatment recommended for COVID-19. Patients infected with COVID-19 rely on their natural immunity and generally seek supportive care to help relieve symptoms. In severe cases, treatment involves mechanical ventilation and vital organ function support.

Thus, an urgent need is there for a composition and method for the treatment of Covid-19 infection in humans.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a composition and method for the treatment of viral infection due to coronaviruses in humans.

It is another object of the present invention that the composition can be orally administered.

It is still another object of the present invention that the production of the compositional can be easily scaled up.

It is still another object of the present invention that the composition can be easily administered.

In one aspect, disclosed is a composition and method for the treatment of infection due to coronaviruses, in particular, Covid-19 viral infection in humans. The compositions can be an oral composition including a methionine cleaving-enzyme. The composition can also include an oral protease inhibitor.

In one aspect, disclosed is a method for the treatment of infection due to coronaviruses, in particular, Covid-19 viral infection in humans including the step of lowering serum methionine levels and inhibiting cellular proteases by orally administering the disclosed composition.

In one aspect, the composition for lowering serum methionine levels includes a recombinant methioninase enzyme that can be orally administered. The cellular proteases can be inhibited by protease inhibitors that can be administered orally and parentally.

In one aspect, the methioninase enzyme can be a recombinant L-methionine α-deamino-γ-mercaptomethane lyase. The protease inhibitor can be a serine- or cysteine-protease inhibitor, or both. One or more protease inhibitors can be given orally or parentally.

In one aspect, the protease inhibitor can be camostat mesylate or E-64d both known in the art.

In one aspect, the methioninase enzyme is a recombinant L-methionine α-deamino-γ-mercaptomethane lyase, the cofactor for methioninase is pyridoxal-L-phosphate that can be administered orally in a fluid, such as drinking water.

In one aspect, the concentration of the pyridoxal-L-phosphate in an aqueous solution can be about twenty (20) millimoles per liter of water.

In one aspect, the dose of methioninase enzymes can be about 10 mg/kg of body weight.

In one aspect, the disclosed is a method of treating coronavirus infection in living beings, the method includes the steps of orally administering a composition including a methioninase enzyme; administering, orally, fluid containing pyridoxal-L-phosphate in a predetermined concentration.

In one aspect, the method may further comprises the step of administering orally or parentally a protease inhibitor in a predetermined concentration.

In one aspect, the pyridoxal-L-phosphate can be orally administered as a solution in drinkable fluid, such as drinking water.

In one aspect, the composition includes the methioninase enzyme. The composition may also include additives, such as flavors, sweeteners, and binders.

In some embodiments, the disclosed composition can be used for treating coronavirus infections in both humans and animals.

The foregoing and other features and advantages of the present invention will be apparent from the following more detailed description of the particular embodiments of the invention.

DETAILED DESCRIPTION

Subject matter will now be described more fully hereinafter using specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods and compositions. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a composition and method for the treatment of coronavirus infections in humans and animals, such as Covid-19 viral infection. The disclosed composition can be orally administered and may not require any strict dietary reductions. Not requiring parental administering can be a particular advantage of the disclosed composition and method, as in severe contagious diseases, such as covid-19 viral infections, the patients can themselves take the medicine.

Disclosed is a method for the treatment of coronavirus infections in living beings. The method includes the steps of orally administering a composition including methioninase enzyme and orally administering a fluid containing pyridoxal-L-phosphate as a cofactor. Optionally, the method may further comprise the step of orally or systemically administering a cysteine- or serine-protease inhibitor. The composition can also include phosphate-buffer saline solution.

The protease inhibitors can be serine or cysteine protease inhibitors that can be both orally and parentally administered. Preferably, in severe acute respiratory distress syndrome, the protease inhibitors can be systemically administered. Also, more than one protease inhibitor can be administered. In case of more than one protease inhibitor is administered, both taken orally, both taken parentally, one taken orally and the other taken parentally are within the scope of the present invention. Both oral or systemic administration of serine or cysteine protease inhibitors can inhibit coronavirus entry into the cells. The protease inhibitors can have a synergistic effect with the methioninase enzyme in the treatment of COVID-19 infection.

The composition including methioninase enzyme can act by lowering the serum methionine levels. It has been scientifically established that the virus-infected cells become methionine addicted. Moreover, the scientific investigations in the art had revealed that coronaviruses require their genome to be methylated, thus are methionine dependent. This novel approach for reducing the multiplication of coronaviruses and treatment of Covid-19 infection in humans and animals has not been explored yet. Additionally, inflammation is the key factor in the spread of infection which can also be the target for the methioninase enzyme since T-cells require excess methionine when activated. Therefore, the disclosed composition can target multiple pathways for decreasing the spread of coronavirus within a living being. Moreover, the disclosed combination of methioninase enzymes with protease inhibitors can have a synergistic effect in the treatment of coronavirus infection. Such a combination can be a powerful cure for patients in severe conditions and probably on life support.

Protease inhibitors, in particular the serine- and cysteine-protease inhibitors are known in the art for both oral and parental administration, and such protease inhibitors are within the scope of the present invention. Serine protease inhibitor camostat mesylate is commercially available that is having good oral bioavailability. E-64d is a known inhibitor of cysteine protease cathepsin B. E-64d can be given alone or in combination with camostat mesylate. E-64d also has good oral bioavailability.

In one exemplary embodiment, the disclosed oral composition can include a methioninase enzyme and one or more oral protease inhibitors. The methioninase enzyme can be a recombinant L-methionine $\alpha$-deamino-$\gamma$-mercaptomethane lyase. The protease inhibitors can include camostat mesylate or E-64d, or a combination thereof. When compared with ip-rMETase, oral rMETase ("o-rMETase") is significantly more effective than ip-rMETase, provided administration of the o-rMETase is accompanied by pyridoxal-L-phosphate ("PLP") in drinking water.

In one exemplary embodiment, disclosed is a method of treating coronavirus infection in living beings including humans and animals. The method includes the steps of orally administering a composition including a methioninase enzyme. The method further includes the step of orally administering pyridoxal-L-phosphate in fluid, such as drinking water. The methioninase enzyme can be recombinant L-methionine $\alpha$-deamino-$\gamma$-mercaptomethane lyase.

In one exemplary embodiment, disclosed is a method of treating coronavirus infection in living beings including humans and animals. The method includes the steps of orally administering a composition including a methioninase enzyme and an oral protease inhibitor. The method further includes the step of orally administering pyridoxal-L-phosphate in fluid, such as drinking water. The methioninase enzyme can be recombinant L-methionine $\alpha$-deamino-$\gamma$-mercaptomethane lyase. Preferably, the protease inhibitor can be a serine or cysteine inhibitor, or a combination thereof. More preferably, the protease inhibitor can be an oral protease inhibitor, such as camostat mesylate and E-64d. It is to be understood that the composition can include more than one protease inhibitor of the same or a different class without departing from the scope of the present invention.

In one exemplary embodiment, disclosed is a method of treating coronavirus infection in leaving beings including humans and animals. The method includes the steps of orally administering a composition including a methioninase enzyme. The method further includes the step of orally or parentally administering a protease inhibitor. The method further includes the step of orally administering pyridoxal-L-phosphate in fluid, such as drinking water. The methioninase enzyme can be recombinant L-methionine $\alpha$-deamino-$\gamma$-mercaptomethane lyase. Preferably, the protease inhibitor can be a serine or cysteine inhibitor, or a combination thereof. Preferably, the protease inhibitor can be an oral protease inhibitor, such as camostat mesylate and E-64d. It is to be understood that more than one protease inhibitor can be administered through different routes.

The embodiments and examples set forth herein were presented to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above and are intended to fall within the scope of the appended claims.

What is claimed is:

1. A method for treating coronavirus infection in an individual in need thereof, the method comprising the steps of:
   administering, orally, an effective amount of a composition comprising methioninase enzyme;
   administering, orally, a fluid comprising an effective amount of pyridoxal-L-phosphates;
   upon administering the methioninase enzyme, administering, orally or parentally, an effective amount of protease inhibitor.

2. The method according to claim 1, wherein the methioninase enzyme is a recombinant L-methionine α-deamino-γ-mercaptomethane lyase.

3. The method according to claim 1, wherein the protease inhibitor is orally administered, the protease inhibitor is a serine- or cysteine-protease inhibitor.

4. The method according to claim 3, wherein a combination of the serine- and cysteine-protease inhibitors are administered.

5. The method according to claim 4, wherein the serine protease inhibitor is camostat mesylate and the cysteine protease inhibitor is E-64d.

6. The method according to claim 1, wherein the protease inhibitor is parentally administered, the protease inhibitor is a serine- or cysteine-protease inhibitor.

7. The method according to claim 6, wherein a combination of the serine- and cysteine-protease inhibitors are administered.

8. The method according to claim 1, wherein the composition further comprises flavors, sweeteners, and binders.

9. The method according to claim 1, wherein the fluid is a solution of pyridoxal-L-phosphate in drinking water.

10. The method according to claim 1, wherein the coronavirus infection is COVID-19 infection.

11. A method for treating coronavirus infection in an individual in need thereof, the method comprises:
    administering, orally, an effective amount of a composition comprising methioninase enzyme and an oral protease inhibitor; and
    administering, orally, a fluid comprising an effective amount of pyridoxal-L-phosphate.

12. The method according to claim 11, wherein the methioninase enzyme is a recombinant L-methionine α-deamino-γ-mercaptomethane lyase.

13. The method according to claim 11, wherein the protease inhibitor is a serine- or cysteine-protease inhibitor.

14. The method according to claim 13, wherein a combination of the serine- and cysteine-protease inhibitors are administered.

15. The method according to claim 14, wherein the serine protease inhibitor is camostat mesylate and the cysteine protease inhibitor is E-64d.

16. The method according to claim 11, wherein the composition further comprises flavors, sweeteners, and binders.

17. The method according to claim 11, wherein the fluid is a solution of pyridoxal-L-phosphate in drinking water.

18. The method according to claim 11, wherein the coronavirus infection is COVID-19 infection.

* * * * *